United States Patent [19]
Bahmanyar et al.

[11] Patent Number: 6,096,028
[45] Date of Patent: Aug. 1, 2000

[54] MULTI-SLOT LASER SURGERY

[75] Inventors: Sina Bahmanyar, Rockford, Ill.; Mark S. Jones, Ballwin, Mo.

[73] Assignee: Alcon Laboratories, Inc.

[21] Appl. No.: 09/124,126

[22] Filed: Jul. 29, 1998

Related U.S. Application Data

[63] Continuation-in-part of application No. 08/556,204, Nov. 9, 1995, Pat. No. 5,921,981.

[51] Int. Cl.⁷ .............................. A61B 3/10; A61B 17/36
[52] U.S. Cl. .................................. 606/4; 606/16
[58] Field of Search .................. 606/4, 5, 6, 10, 606/11, 12, 14, 15, 16, 17, 19; 372/108

[56] References Cited

U.S. PATENT DOCUMENTS

| | | | |
|---|---|---|---|
| 4,477,159 | 10/1984 | Mizuno et al | 351/221 |
| 4,719,912 | 1/1988 | Weinberg | 606/4 |
| 4,830,483 | 5/1989 | Kohayakawa et al. | 606/4 |
| 5,007,729 | 4/1991 | Erickson et al. | 351/219 |
| 5,067,951 | 11/1991 | Greve | 606/4 |
| 5,189,450 | 2/1993 | Crossman et al. | 351/219 |
| 5,300,062 | 4/1994 | Ueno | 606/4 |
| 5,309,187 | 5/1994 | Crossman et al. | 351/219 |
| 5,318,022 | 6/1994 | Taboada et al. | 128/633 |

*Primary Examiner*—Linda C. M. Dvorak
*Assistant Examiner*—Sonya Han Oguyu
*Attorney, Agent, or Firm*—Jeffrey S. Schira

[57] ABSTRACT

Various embodiments of optical fiber cables and laser probes are disclosed for providing multi-spot laser beams from a single laser beam source. This permits time-intensive but repetitive laser surgical procedures such as panretinal photocoagulation to be performed with increased accuracy and in a fraction of the time currently allotted for such procedures.

10 Claims, 10 Drawing Sheets

MULTI-SLOT LASER SURGERY

CROSS-REFERENCE TO RELATED APPLICATIONS

This application is a continuation-in-part of Ser. No. 08/556,204 filed Nov. 9, 1995 now U.S. Pat. No. 5,921,981.

STATEMENT REGARDING FEDERALLY SPONSORED RESEARCH OR DEVELOPMENT

Not Applicable.

BACKGROUND OF THE INVENTION

This invention relates to laser ophthalmic surgery and more particularly to a method and system particularly suited to panretinal photocoagulation procedures performed on a human patient.

Photocoagulation has been used for various ophthalmic procedures such as panretinal photocoagulation (PRP) and the like. Such procedures are performed using either a slit-lamp (SL) laser delivery system or, when surgical intervention is required, endo-ocular laser probes.

In the slit-lamp system, laser energy is delivered from the laser source to the imaging optics via a single optical fiber. As is known, the imaging optics are used in conjunction with a variety of contact lenses, and must be capable of focusing the output end (distal) of the fiber onto the retina. The focal length of the imaging optics, is typically variable, i.e. zoom, to magnify the size of the fiber's image on the retina from 1 to 20 times, corresponding to 50–1000 microns on the retina.

Current SL systems offer a single fiber for single point exposure on the surgical area. The surgeon positions the fiber image to the desired location by observing a low energy aiming beam on the treatment area. By turning the laser on/off and moving the aiming beam, the surgeon can lay down a pattern of spots on the treatment area. The number of spots is determined by the size of the treatment area and the laser spot size desired. For photocoagulation of microaneurysms on the retina, the laser spot size must be small (<100 microns) to avoid damage to surrounding tissue.

For medical conditions which require panretinal photocoagulation (PRP), also known as scatter photocoagulation, the area affected may include the entire retina outside the foveal region. The accepted mode of treatment is to lay down an uniform distribution of photocoagulative burns, with spot sizes of 250–500 microns and spaced at 1 times the spot diameter. A typical treatment consist of 1600 burns. The time to position the spot and deliver the laser energy depends on the features of the SL and the skill of the surgeon and is typically 2 seconds per spot. This means that the treatment time is in excess of 60 minutes which is fatiguing to the patient and surgeon. Also, laying down a uniform pattern is difficult and the pattern is typically more random than geometric in distribution.

When PRP treatment requires surgical intervention, the SL is not used. Instead standard endoocular laser probes are employed. The treatment objectives are the same, however, to lay down a pattern of photocoagulative burns in the affected area. Using the endo-laser probe, the surgeon holds the distal tip close to the retina and lays down 1500–2000 spots, 500 microns in diameter. This procedure can take more than one hour. Using the probe close to the retina increases the risk of accidental tears and the length of the procedure prolongs the anesthesia time in high risk patient groups.

SUMMARY OF THE INVENTION

Among the various objects and features of the present invention may be noted the provision of an apparatus and method which facilitates ophthalmic operations such as panretinal photocoagulation.

Another object is the provision of such an apparatus and method which significantly reduces the time required for such operations.

A third object is the provision of such an apparatus and method which is readily usable with existing equipment.

A fourth object is the provision of such an apparatus and method which provides increased accuracy.

A fifth object is the provision of such an apparatus and method which provides a more repeatable pattern of laser spots or burns.

Other objects and features will be in part apparent and in part pointed out hereinafter.

BRIEF DESCRIPTION OF THE DRAWINGS

Similar reference characters indicate similar parts throughout the several views of the drawings.

DESCRIPTION OF THE PREFERRED EMBODIMENT

Figure 1:
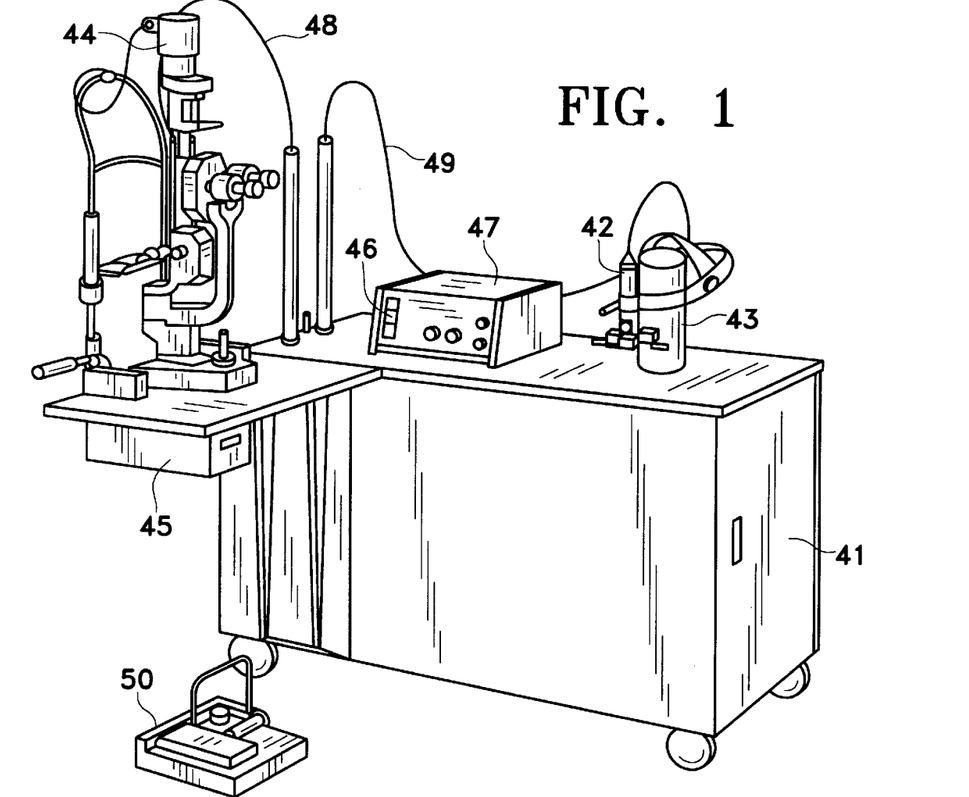
FIG. 1 is a perspective view of a slit-lamp laser system incorporating the present invention.
Figure 2:
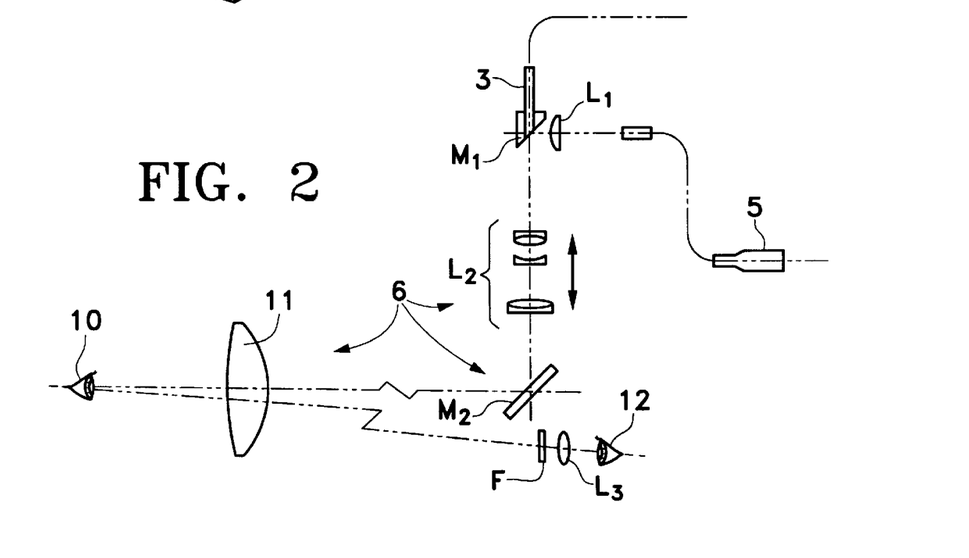
FIG. 2 is a simplified illustration of the optics of the system of FIG. 1.

In a first embodiment of the present invention, the ophthalmic operation is performed using a slit-lamp apparatus, such as that shown in FIGS. 1 and 2. The physician performing such an operation uses such apparatus to control the application (and intensity) of illuminating light and the application (and intensity) of laser energy to the treatment/operative site. Specifically, such apparatus includes an optical fiber device 3 for transmitting a laser beam coming from a laser source, and a second optical fiber device 5 for transmitting the illumination light from a light source. A lens holder unit 6 is provided for accommodating therein a lens system for transmitting the laser beam and the illumination light to the patient's eye 10. The optical system includes an ophthalmoscope lens 11 for magnifying the image of the fundus oculi of the patient's eye. This image is thereby provided to the eye 12 of the physician.

Referring more specifically to FIG. 2, the optical system includes a focusing lens L1 for the illumination light and a perforated mirror M1. These two components are arranged such that the laser beam travels generally along the optical path of the illumination light. (As will become apparent, the laser beam at this point is actually a composite beam, and it is the composite beam which travels along the optical path defined by the optics discussed below to the patient's eye.) It is possible to use a half mirror or a dichroic mirror in place of the perforated mirror M1.

The laser beam and the illumination light coaxial therewith are projected on the patient's eye by mean of a projection lens L2. The size of the spot of the laser beam imaging on the fundus oculi is changed by moving the projection lens L2 in the direction of optical axis. A mirror M2 is housed in the aforementioned lens holder unit 6 together with the aforementioned lens L1 and the mirror M1. A filter F for protecting the physician's eye 12 is adapted to be placed out of the path of light during the observation and the sighting, but is moved into the path of light in advance of the laser operation. A lens L3 is used for observing the image of the patient's eye.

FIG. 1 shows a slit-lamp in combination with a binocular indirect ophthalmoscope for permitting a switching of the laser beam. Specifically, a laser source housing 41 encases a laser tube, a laser control system and so forth. The binocular indirect ophthalmoscope 42 is mounted on a carrier 43. A slitlamp 44 is adapted to be moved up and down by means of a slit table 45. In conventional manner, changeover switches 46 and a control box 47 are provided, control box 47 controlling various conditions such as, for example, coagulation time, coagulation power and spot size of the laser beam. Optical cables 48, 49 for the laser beam are connected to ophthalmoscope 42 and to the slitlamp 44 respectively. A foot switch device 50 has two pedals for triggering the optical coagulation and for triggering the vertical movement of the slit table 45 respectively. It should be understood that also the slit-lamp system is shown and described in some detail, the present invention is not limited to any particular slit-lamp system.

Figure 3:
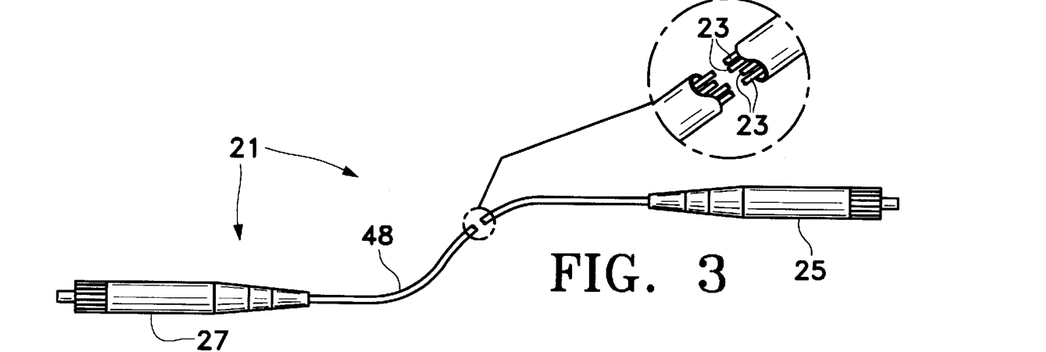
FIG. 3 is an elevation of an optical fiber cable used in the system of FIG. 1.

Referring now to FIG. 3, there is shown a multi-spot laser delivery system 21 of the present invention. It is preferred in this system that optical fiber cable 48 be a multiple-fiber assembly, with the result that multiple spots can be imaged onto the treatment area. Moreover, the spacing of the fibers can be optimized to yield a more uniform geometric pattern. The surgeon using the system of FIGS. 1 and 2 can position the multi-spot pattern using the low power aiming beam and deliver the photocoagulative laser pulse. The time to position the multi-spot pattern is the same as the single spot procedure used in the prior art. However, the total treatment time is reduced by the number of spots in the pattern. As an example, if four (4) spots (as indicated in FIG. 3 by the four separate optical fibers 23) are used the treatment time is potentially reduced to one fourth the standard time.

Figure 3A:
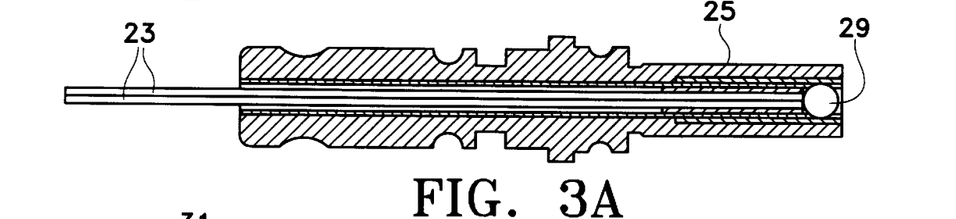
FIG. 3A is a cross-sectional view of a proximal connector of the optical fiber cable of FIG. 3.
Figures 3B, 4, 4A, 4B:
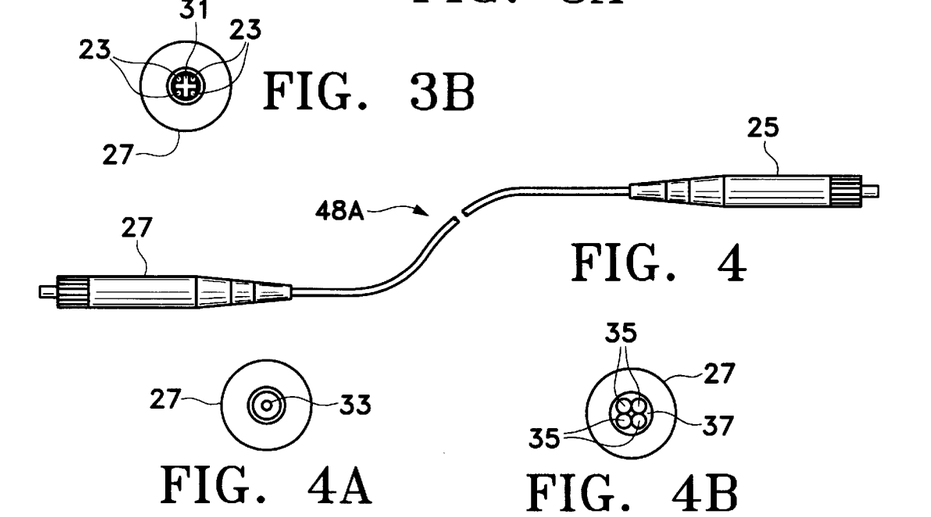
FIG. 3B is an end view of the distal connector of the optical fiber cable of FIG. 3.
FIG. 4 is an elevation of an alternative embodiment of the optical fiber cable used in the system of FIG. 1.
FIG. 4A is an end view of a distal connector of the optical fiber cable of FIG. 4, with parts removed for clarity.
FIG. 4B is an end view similar to FIG. 4A with the removed parts reinserted.
Figure 4C:
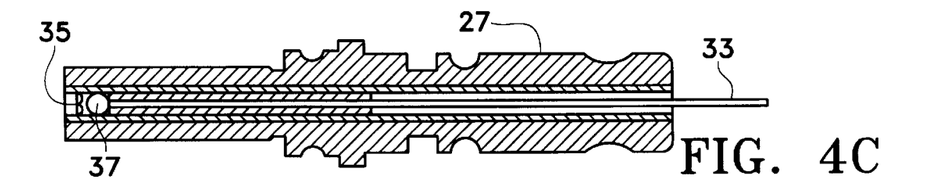
FIG. 4C is a longitudinal sectional view of the distal connector of the optical fiber cable of FIG. 4.

Optical fiber cable 48 is constructed of four fibers 23 connected to the laser source via a proximal connector 25 (input end) and to the slit lamp imaging optics described above via a distal connector 27 (output end). The size of the fiber is chosen for the highest core to cladding diameter ratio for optimum energy collection at the proximal end. The maximum size of the fiber is governed by the magnification range of the imaging optics in the slit lamp and the desired spot size on the retina. Magnification ranges for standard SL imaging optics are 1:1 to 20:1. If the fibers selected are 200 microns in diameter, the imaging size on the retina would vary from 200–4000 microns. For PRP procedures, the surgeon typically uses a 500 micron spot. To insure uniform input of laser energy into the fibers, a lens 29 is provided in the optical path in the proximal connector. The lens shown is a ball lens; however, other types of focusing elements could be used.

A star spacer 31 is used at the distal end of distal connector 27 to provide a uniform spacing of two (2) times the spot diameter. The spacer can be metallic, ceramic, etc., or the fibers can be held in spaced relationship in an epoxy matrix material.

Referring to FIG. 4, an alternative optical cable assembly 48A for use with a slit-lamp assembly is shown. In cable 48A, there is a single fiber 33 optically connected to the laser source via proximal connector 25 (input end) and to the slit lamp imaging optics via distal connector 27 (output end).

The proximal end of fiber 33 is a standard polished end fiber with no additional lenses. The distal end contains a microlens array 35 with four elements to produce four spots. A collimating lens 37 provides uniform light energy to the microlens array. The size of the fiber is chosen for the optimum energy collection at the distal end of the fiber. The lenses shown are a ball lens and a 4-element microlens array; however, other types of focusing elements could be used. The single laser beam transmitted by fiber 33 is collimated by lens 37 and split into four simultaneous parallel laser beams by microlens array 35 for application through the slit-lamp apparatus to the patient.

Figure 5:
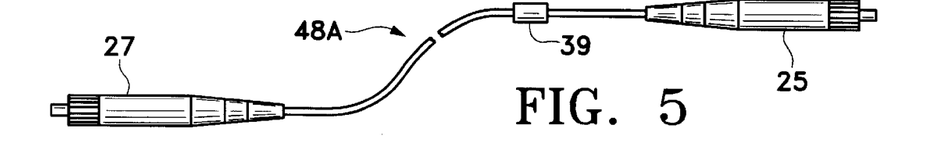
FIG. 5 is an elevation of a third embodiment of the optical fiber cable used in the system of FIG. 1.

Referring to FIG. 5, another alternative construction of cable 48, labeled 48B, is illustrated. In this construction, the single laser beam from the source is split using fiber splitters. Specifically, in the embodiment shown in FIG. 5, cable 48B has a single optical fiber 33 connected to the laser source via proximal connector 25, which is multiplexed by means of a 1×4 multimode coupler 39 into four fibers 23 at the distal end. The proximal end is a standard polished end fiber with no additional lenses. Inside the multimode coupler the single fiber is multiplexed into four fibers via three 1:2 fiber splitters (disposed in a configuration such as that shown in FIG. 8A). Of course the actual method of splitting may be varied as desired.

Figures 5A, 5B, 6:
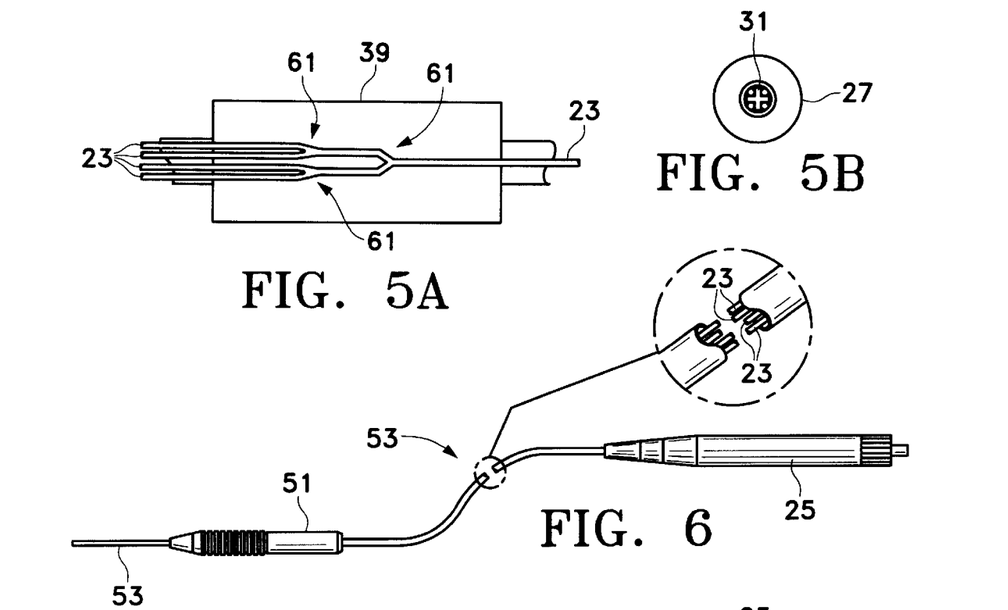
FIG. 5A is an enlarged view with parts broken away for clarity of the optical fiber cable of FIG. 5.
FIG. 5B is an end view of the distal connector of the optical fiber cable of FIG. 5.
FIG. 6 is an elevation of a laser probe of the present invention adapted for ophthalmic surgical procedures such as panretinal photocoagulation.
Figure 6A:
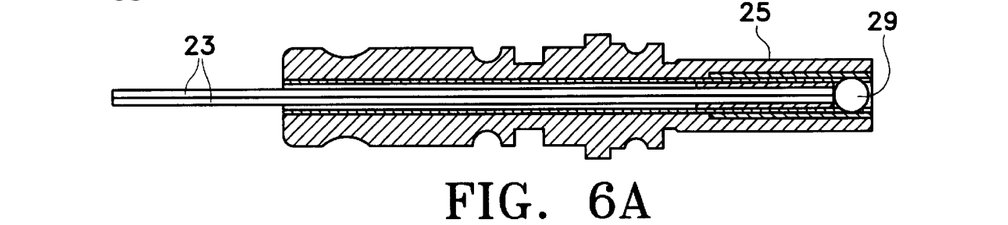
FIG. 6A is a cross sectional view of the proximal connector of the laser probe of FIG. 6.
Figure 6B:
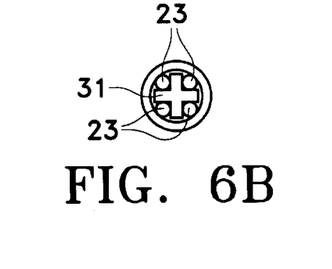
FIG. 6B is a distal end view of the probe of FIG. 6, with parts removed for clarity.
Figure 6C:
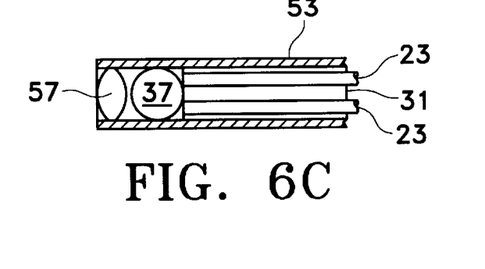
FIG. 6C is a cross sectional view of the distal end of the probe of FIG. 6.

The maximum size of the fiber is governed by the magnification range of the imaging optics in the slit lamp and the desired spot size on the retina. Magnification ranges for standard SL imaging optics are 1:1 to 20:1. If the fibers selected are 200 microns in diameter, the imaging size on the retina would vary from 200–4000 microns, as desired by the physician. Star spacer 31 is preferably used at the distal end to provide the desired spacing between the spots by holding the fibers 23 in fixed geometrical relationship.

Figure 7:
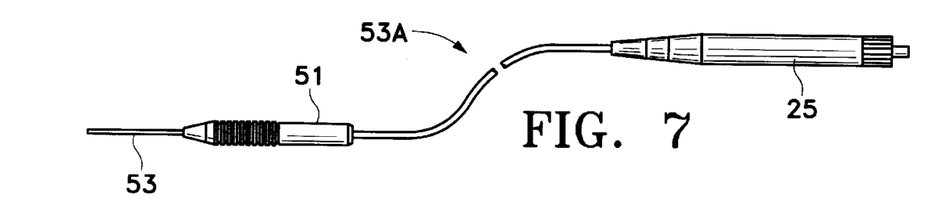
FIG. 7 is an elevation of an alternative embodiment of the laser probe of FIG. 6.
Figure 8:
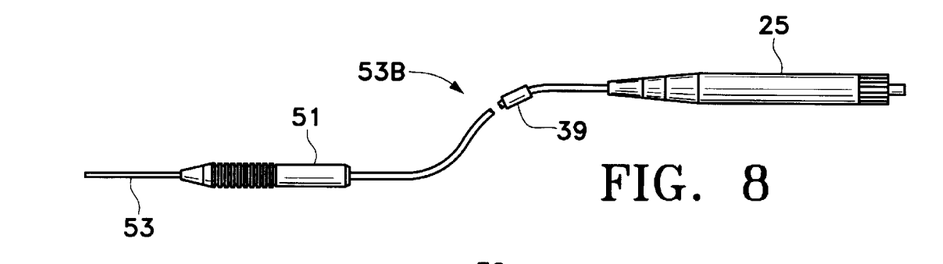
FIG. 8 is an elevation of a third embodiment of the laser probe of FIG. 6.
Figure 8A:
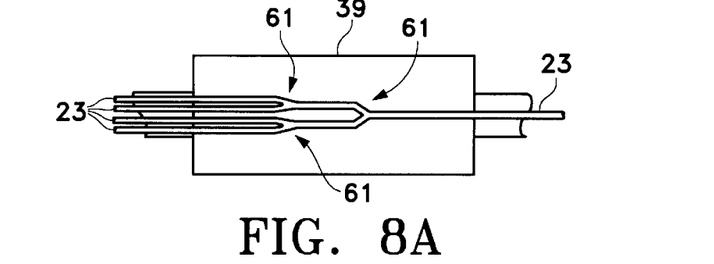
FIG. 8A is an enlarged view of a portion of the probe of FIG. 8.
Figure 8B:
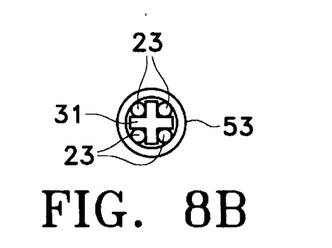
FIG. 8B is a distal end view of the probe of FIG. 8, with parts removed for clarity.
Figure 8C:
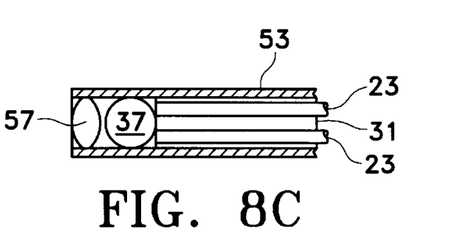
FIG. 8C is a cross sectional view of the distal end of the probe of FIG. 8.

As discussed above, when PRP treatment requires surgical intervention, the slit-lamp assembly of FIGS. 1 and 2 is not used. Rather endo-ocular laser probes such as those shown in FIGS. 6–8 are utilized. The optical constructions of these probes are very similar to the optical cable constructions discussed above. Rather than a distal connector, however, such probes have a handpiece 51, generally terminating in a distal needle 53.

By replacing the existing single fiber endo-laser probe with a multiple fiber probe (or other beam splitting devices discussed below), multiple spots are imaged onto the treatment area. The spacing of the fibers (and/or beams) can be optimized to yield a more uniform geometric pattern than is available with conventional equipment. The surgeon can position the multi-spot pattern using the low power aiming beam and deliver the photocoagulative laser pulse. The time to position the multi-spot pattern is generally the same as the single spot procedure, but the total treatment time is reduced by the number of spots in the pattern, similar to the reduction discussed above in connection with the slit-lamp system.

In FIG. 6, a probe 53 is constructed of four fibers 23 connected to the laser source via proximal connector 25. Fibers 23 run the entire length of probe 53 and terminate distally in handpiece 51. The size of the fibers is chosen for the highest core to clad diameter ratio for optimum energy collection at the proximal end. To insure uniform input of laser energy into the fibers, lens 29 is provided at the proximal end. Although the lens shown is a ball lens, other types of focusing elements could be used. Star spacer 31 is used at the distal end to provide the desired spacing of the fibers and to hold them in fixed geometrical relationship. A collimating lens 37 and/or a focusing lens 57 are preferably disposed distally of the fibers 23 to more accurately direct the resulting simultaneous laser beams.

Figure 7A:
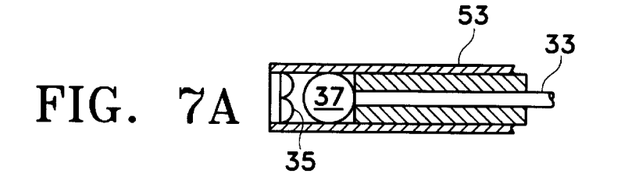
FIG. 7A is a cross sectional view of the distal end of the probe of FIG. 7.

In FIG. 7, an alternative embodiment 53A of the laser probe is shown. In this embodiment, the probe uses a single fiber 33 connected to the laser source via proximal connector, which fiber continues to the distal needle end of handpiece 51. The proximal end of fiber 33 is a standard polished end fiber with no additional lenses. The distal end terminates at a microlens array 35 having four elements to produce four spots at a distance to minimize risk of retinal tears. A collimating lens 37 provides uniform light energy to the microlens array. The lenses shown here are a ball lens and a 4-element microlens array, however, other types of focusing elements could be used.

In FIG. 8, a third embodiment 53B of the laser probe is shown. In this embodiment, a single fiber 33 is connected to the laser source via proximal connector 25 and is multiplexed by a 1×4 multimode coupler 39 into four fibers 23 at the distal end. The proximal end is a standard polished end fiber with no additional lenses. Inside the multimode coupler the single fiber is multiplexed into four fiber via three 1:2 fiber splitters 61, or by any other suitable method. The size of the spot and spot spacing vary proportionally with the distance from the distal tip to the retina. A star spacer 31 is used at the distal end to suitably space fibers 23. A collimating lens 37 and a focusing lens 57 may be provided distally to suitably focus the simultaneous laser beams at a distance from the distal end of the handpiece needle to help avoid the possibility of retinal tears.

Although the present invention makes significant improvements to the apparatus and methods currently being used for PRP, there are some instances in which it could be further improved. For example, physicians may desire to perform both single spot and multi-spot treatments on the same patient. It would therefore be desirable to have a multi-spot apparatus which could be switched as desired to a single-spot mode of operation. It is preferred to implement such a function by adding a switching or selecting mechanism in the optical path to provide the desired selectable single-spot or multi-spot operation. Several embodiments of such selecting mechanisms are described below. It has been discovered that the most convenient positions for such selecting mechanisms are at the entrance or exit ends of the optical cable(s). Both alternatives are described below.

Figure 9:
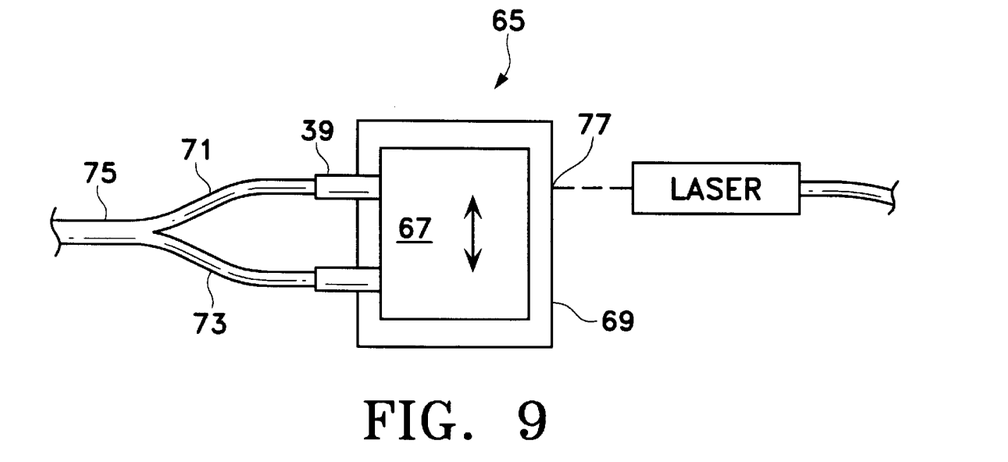
FIG. 9 is an elevation of another embodiment of the present invention which facilitates switching back and forth between single spot and multi-spot operation.
Figure 9A:
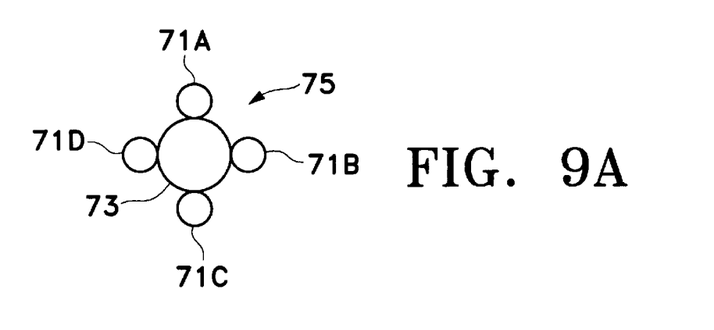
FIG. 9A illustrates the distal end of the fiber cable of FIG. 9, with parts broken away for clarity.

One embodiment of a selecting mechanism is shown in FIG. 9. In this embodiment, a selection mechanism 65 includes a translating member 67 which is movable between first and second positions with respect to a base 69. The translating member or mechanism 67 holds two 50 uM fibers (not shown), the first of which is connected to a 1:4 fiber optic coupler 39 which equally divides the laser energy into four beams which are supplied via a four fiber cable 71. The second fiber is not split, but rather is supplied via a cable 73 to a composite cable 75. The exit end of the cable 75 is illustrated in FIG. 9A, which shows that the four fibers 71A–D of cable 71 are positioned uniformly around the distal end of the monolithic fiber 73 at the exit end of composite cable 75. The translating mechanism 67 at the entrance end is used to position the single-output fiber 73 or the multi-spot fiber 71 at the focus 77 of the laser. By activating the translating mechanism, the user can select between a single spot or multiple spot output.

Figure 10:
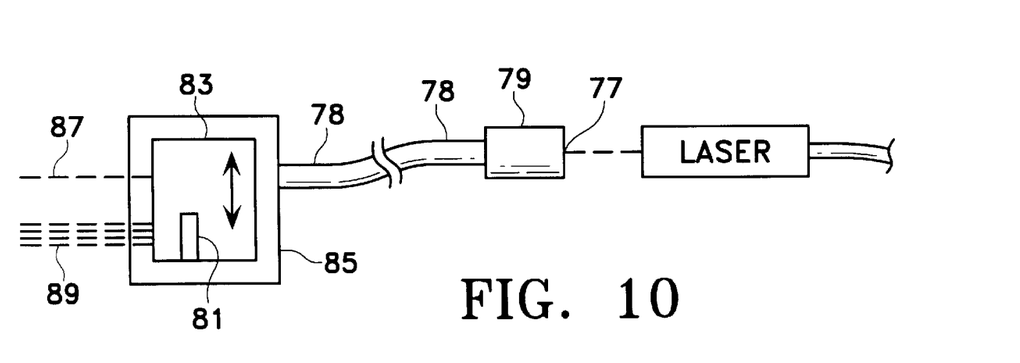
FIG. 10 illustrates an alternative embodiment to that of FIG. 9.

The exit end embodiment of FIG. 10 is similar. In this embodiment, used when the exit end of the slit lamp is more readily accessible, a single 50 uM fiber 78 is mounted in the entrance end connector 79 at the focus 77 of the laser. At the exit end, a multi-spot lens element 81 is mounted to a translating mechanism 83. The translating mechanism is movable with respect to a base 85 so as to choose either single spot output (indicated by dashed line 87) or, through the lens element 81, multi-spot output (indicated by dashed lines 89). By activating the translating mechanism, the user can select between single or multiple spots. The lens element may be a four-segment circular prism or a diffractive lens element. The diffractive element is preferred because of its insensitivity to lateral positioning errors and because of its automatic focus compensation.

It should be realized that a circular prism or diffractive lens element can also be used in connection with a laser probe to divide a single laser beam into multiple spots at the distal end of the probe. In this case it is sometimes desirable to include an additional optical element to focus the resulting pattern onto the retina. Alternatively, the diffractive element itself may perform this function. It is also preferred that the distal surface of the distalmost optical element be flat so that imaging in air or a fluid-filled eye will produce the same pattern.

Figure 11:
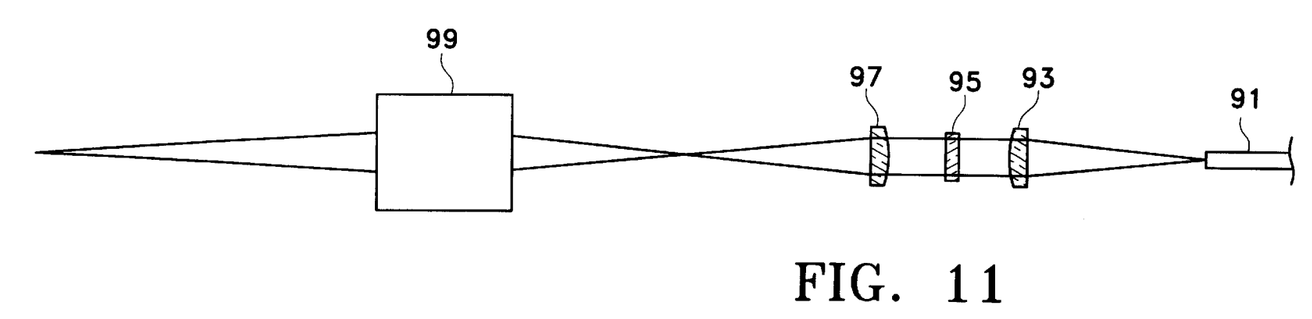
FIG. 11 is a schematic illustrating the operation of the present invention in connection with the zoom system of a slit lamp.

A preferred configuration for using a diffractive lens element in connection with a slit lamp assembly is shown in FIG. 11. In this configuration a 50 micron fiber 91 supplies laser energy to a collimating lens 93. The collimated light is passed through the diffractive lens element 95, and subsequently passes through a refocusing lens 97. The collimating lens collimates the energy from the 50 micron fiber and the refocusing lens forms the image of the fiber at the focal plane of an imaging (zoom) lens 99 of the slit lamp system. One advantage of this configuration is that the diffractive lens element 95 can be inserted or withdrawn form the collimated space without changing the focus position of the other lenses. When inserted, element 95 divides the image of the fiber into four equal parts, allowing the zoom lens to form four images in the same focal plane. It is preferred that the diffractive lens element be formed on or in a clear optical substrate. The output of refocusing lens 97 is preferably four spots spaced in a square pattern, separated by one to two times the diameter of a single spot.

Figure 12:
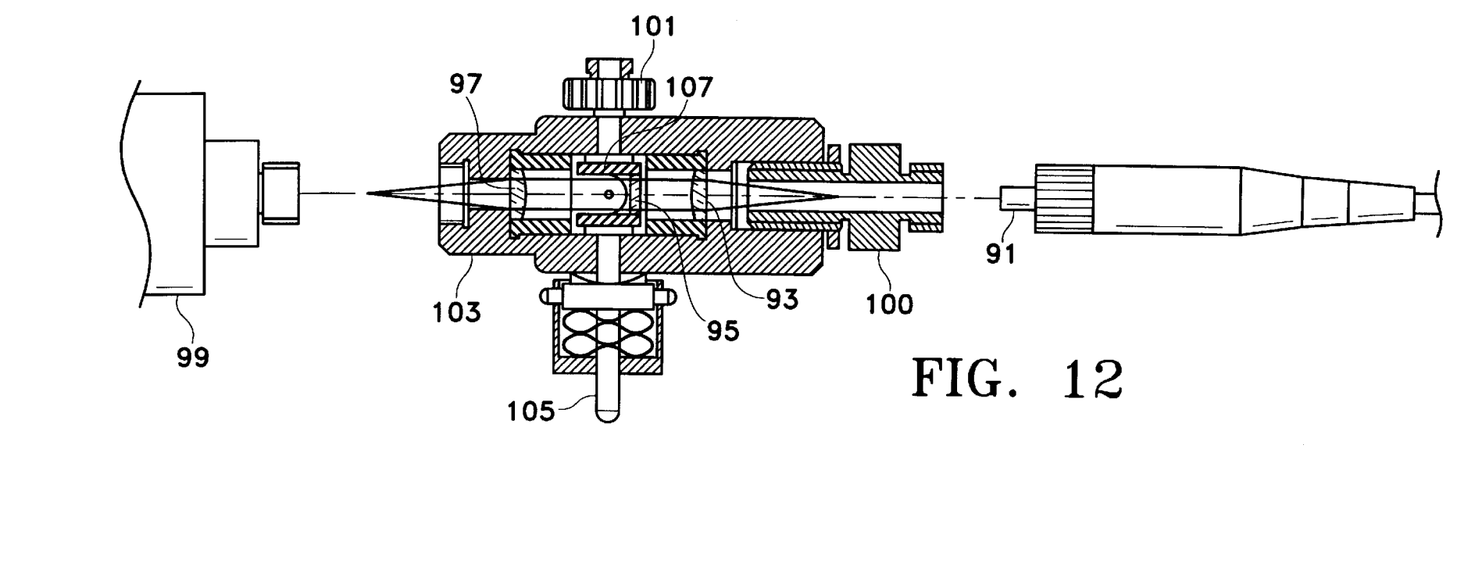
FIG. 12 is a cross-sectional view of an embodiment of the invention of FIG. 11.

The configuration of FIG. 11 is shown in more detail in FIG. 12. Although the configuration shown illustrates the use of a standard SMA-type connector 100, the present invention is not limited to the use of any particular connection. The particular design of FIG. 12 enables the user to easily select between single or multi-spot operation by rotating a knob 101 on the side of an adapter housing 103. Knob 101 turns a shaft 105 on which is mounted a single/multi-spot lens cage 107 which holds diffractive element 95. By rotating the knob, and thus rotating the shaft, the user can insert or remove the diffractive lens element 95 from the optical path at will. Note that the lens cage has several sides, each of which could be used to hold a different multi-spot lens. These different lens can be selected to have a different number of spots or to direct the spots into different geometric patterns (i.e., square, rectangle, triangle, line, etc.). When different lens elements are used on the different sides of the lens cage, these patterns can be changed by the user at will.

It is preferred that the collimating and refocusing lens have the same focal length, thereby producing a 1:1 relay system. In this manner the size of the spot(s) generated by the optical system will be the same as those in the zoom system without the multi-spot feature.

Figure 13:
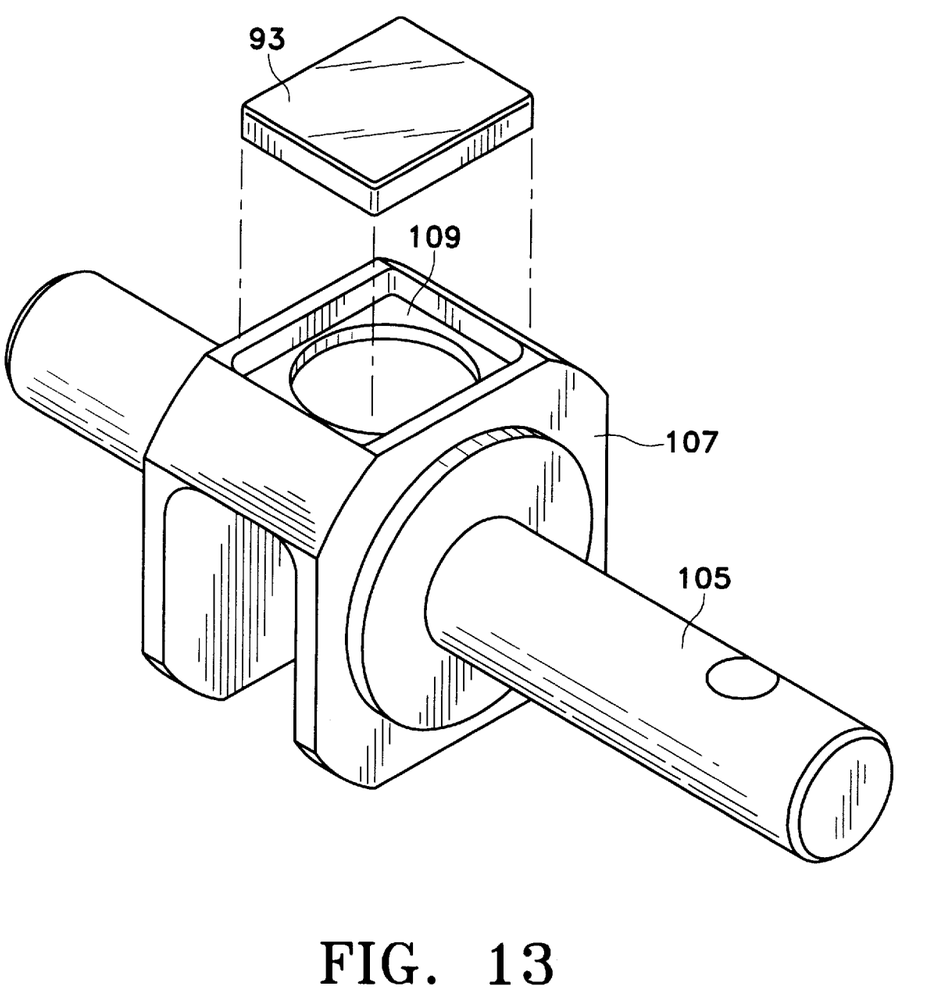
FIG. 13 is a perspective view of a portion of the mechanism for changing the output of the invention of claim 9 from single spot to multi-spot.

The lens cage 107 is illustrated in FIG. 13. More particularly, lens cage 107 is seen to have a recess 109 for receiving diffractive lens element 93. The recess is off-center with respect to the shaft, so that the element 93 may be rotated into and out of the path of the laser energy as desired. When the multi-spot lens is inserted into the optical path, a multi-spot pattern is generated. When it is rotated out of the path, a single spot is formed. Of course, additional recesses and sides could be provided to allow for additional lens elements as described above.

It has been found that an eight-phase level grating works satisfactory for diffractive lens element 93. That grating suppresses higher order harmonics in the diffraction pattern and is capable of high efficiency. Of course, if even greater suppression is desired, a spatial pinhole filter (not shown) can be positioned in the optical path coincident with the zoom optic focal point. This mechanical pinhole would block (spatially filter) the higher order diffraction patterns from reaching the retina.

Figure 14:
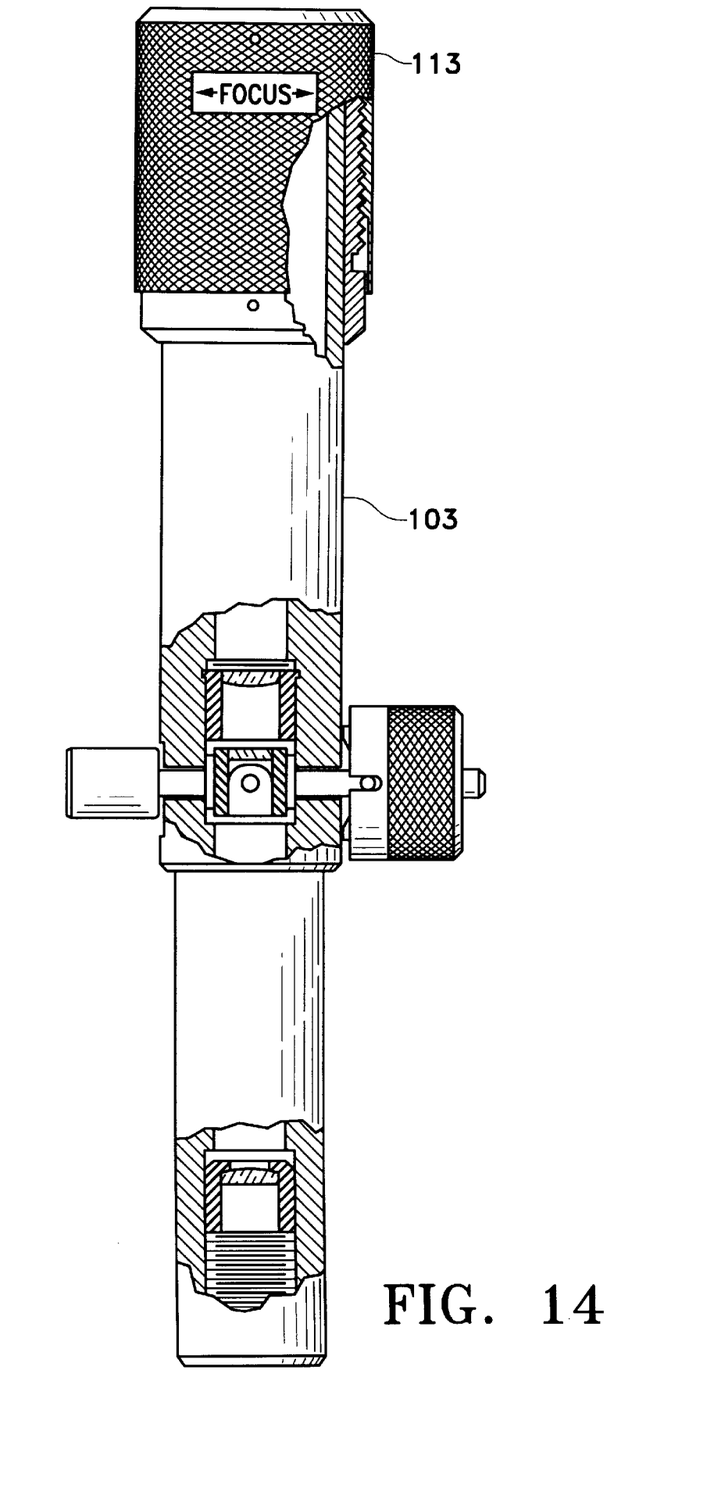
FIG. 14 is an elevation of an embodiment of the present invention which is operable with non-parfocal slit lamp systems.

It has been found that some slit lamp zoom systems are non-parfocal. For these systems, during at least a portion of the magnification range the increase in image size is achieved by defocusing the image. To correct this, the system of FIG. 14 has been designed to longitudinally shift the distal end of the fiber to refocus the multi-spot pattern onto the retina. More specifically, the system of FIG. 14 includes a focus ring 113 adjustably secured to housing body 103 by suitable screw threads as shown. Rotation of the focus ring changes the length of the optical path. It is adjusted until the pattern is suitably focused on the retina. This particular solution to the problem of non-parfocal slit lamp zoom systems does, however, suffer from the fact that the image size of the multiple spots on the retina is reduced.

An alternative solution is to select a diffractive lens element which has a larger spot to spot spacing at lower zoom magnifications but has the desired spacing in the magnification of interest. For example, an element which spaces the spots somewhat further apart at 50 micron spot size, but spaces them at approximately the spot size in the range of interest (200–400 microns) is preferred. Although the spots under this approach are somewhat blurred, the spacing is roughly correct and operation is satisfactory.

Figures 15, 16:
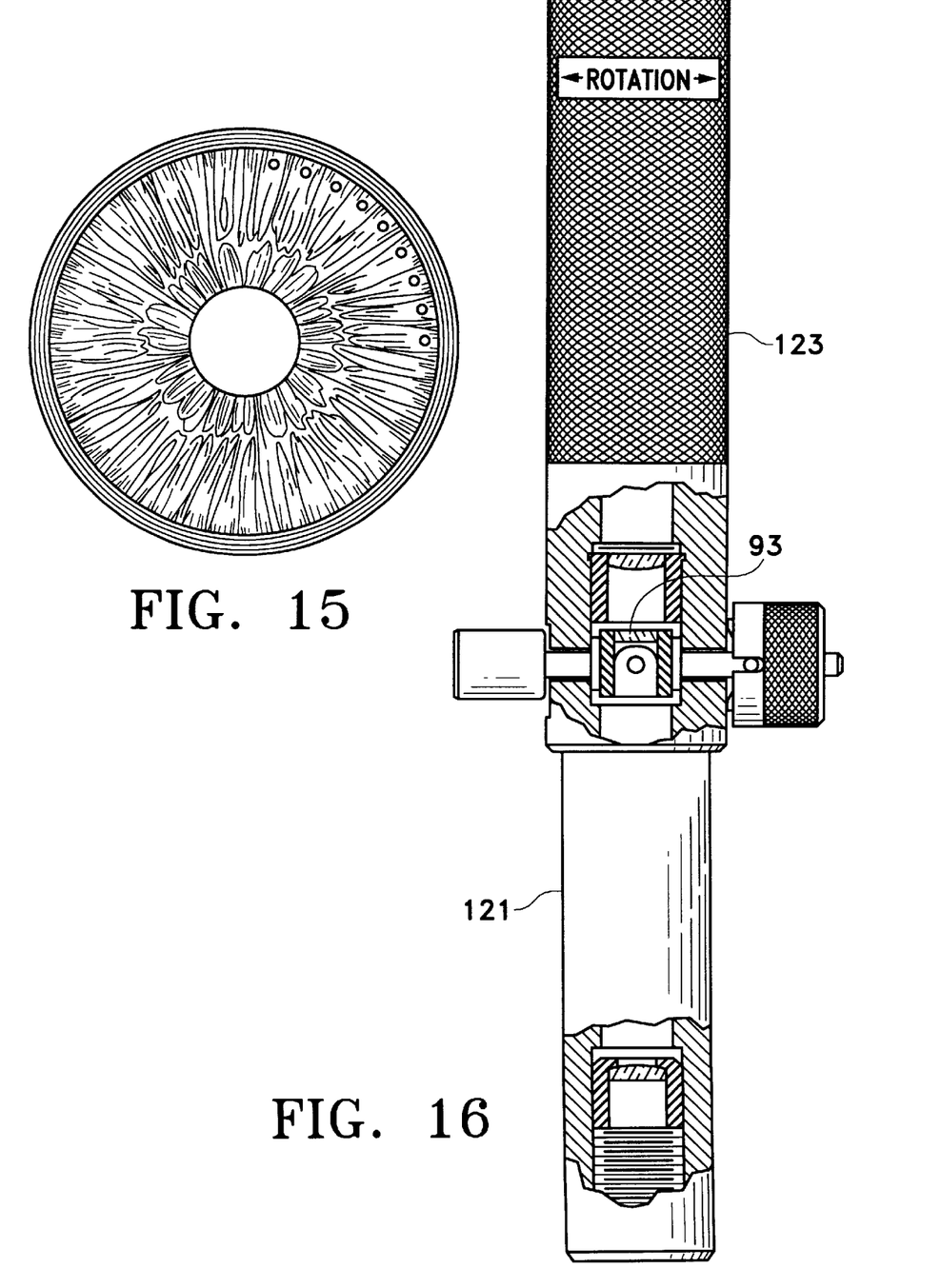
FIG. 15 is an elevation illustration a multi-spot laser procedure on an eye.
FIG. 16 is an elevation of an embodiment of the present invention particularly suited for use in the procedure of FIG. 15.

It is known that for glaucoma treatment, laser burns (holes) are placed in the iris (gonioplasty) or trablicular meshwork. This is illustrated in FIG. 15. In this procedure, the laser bursn are typically placed in an arc centered around the pupil. It would be desirable to simplify this operation. To that end, the system of FIG. 16 has been designed. In this system, the input laser fiber is connected to a fixed housing member 121. The knob 101/lens cage 107 arrangement described above is disposed in a rotatable housing member 123 which is rotatably secured to the fixed housing member. In this embodiment, it is preferred that the diffractive lens element 93 generate only a pair of spots. The rotatable upper portion 123 may be rotated by the surgeon as desired to rotate the pattern of the pair of spots. In this way, the surgeon can easily form the pattern of laser burns shown in FIG. 15 at roughly twice the rate which is currently achieved.

Figure 17:
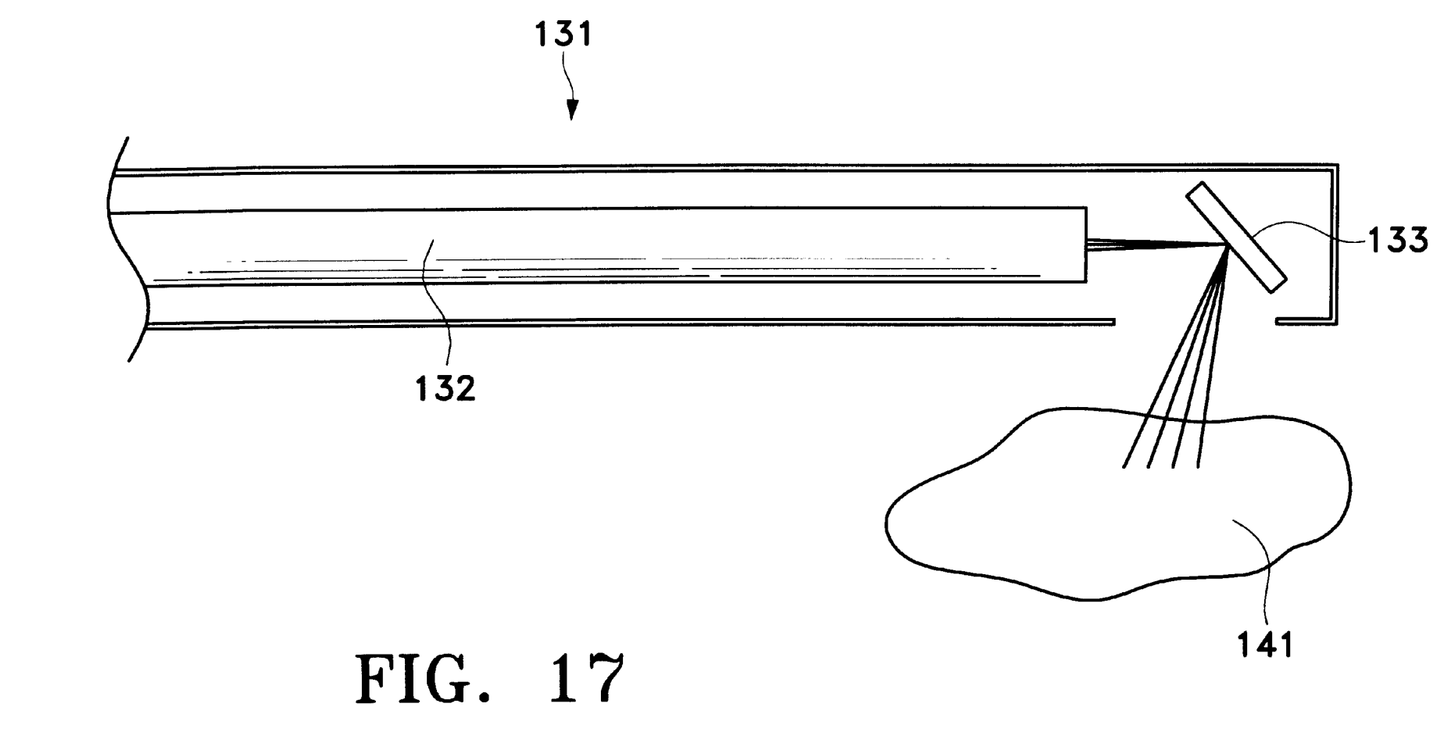
FIG. 17 is a simplified elevation of a side firing endo-laser probe of the present invention.

Referring now to FIG. 17, there is illustrated an endolaser probe 131 which is particularly suited for directing a multi-spot pattern in a direction not on the axis of the fiber. For example, it can be desirable to provide such a pattern at right angles to the axis of the probe, or even at retro-reflected (>90 degree) angles. Side firing fibers are used, for example to ablate tissue in benign prostate hyperplasia. This can be readily accomplished with the probe 131 of FIG. 17. In this probe, the laser energy from the laser fiber 132 impinges upon a reflective diffractive grating 133. The reflective diffractive grating not only reflects the laser energy to the desired location 141, but also provides a multi-spot output. This significantly reduces the time necessary to perform the procedure. It also permits the use of laser photocoagulation in places which otherwise cannot be reached easily or at all, such as at the extreme edges of the retina.

It should be understood that the present invention does not depend on the particular type of laser being used, although the materials making up the optical fibers could be optimized for particular laser types. It is desired, however, that if practicable the optical fibers be chosen to have an optimum core to clad ratio. Various lens types, such as Gradient-Index (GRIN), ball diffractive, holographic, microlenslets, or any combination thereof may be used without changing the underlying invention. Moreover, although the invention has been described in connection with ophthalmic surgery, and in particular in connection with PRP, it should be understood that the invention may also have application to other procedures such as corneal ablation and/or cutting and dermatology.

What is claimed is:

1. A laser probe assembly, comprising:
    a proximal connector adapted for connection to a laser source, the laser source generating a single beam of laser energy;
    a handpiece having a distal end sized for purposes of performing a surgical procedure;
    an optical fiber cable extending from the proximal connector to the handpiece; and
    a reflective diffractive element disposed distally of a distal end of the optical fiber cable between the laser source and the distal end of the handpiece and between the laser source and the distal end of the handpiece for splitting the single beam of energy into a plurality of simultaneous laser beams so that the simultaneous laser beams exit adjacent the distal end of the handpiece generally parallel to each other, the simultaneous laser beams, upon exiting from the handpiece, having a size suitable for performing the surgical procedure.

2. The laser probe assembly of claim 1 wherein the optical fiber cable includes a plurality of optical fibers, there being one optical fiber per simultaneous laser beam in the optical fiber cable.

3. The laser probe assembly of claim 2 further including a means disposed at the distal end of the optical fiber cable for holding the plurality of optical fibers in fixed geometrical relationship.

4. The laser probe assembly for an ophthalmic surgical procedure as set forth in claim 3 wherein the holding means is a star spacer.

5. The laser probe assembly for an ophthalmic surgical procedure as set forth in claim 3 wherein the plurality of optical fibers are held in the fixed geometrical relationship by an adhesive.

6. The laser probe assembly for an ophthalmic surgical procedure as set forth in claim 2 wherein the optical fiber cable includes at least one fiber splitter.

7. The laser probe assembly for an ophthalmic surgical procedure as set forth in claim 6 wherein the fiber splitter is disposed intermediate the proximal and distal ends of the optical fiber cable.

8. The laser probe assembly of claim 1 further including a focusing element disposed between the laser source and a proximal end of the optical fiber cable.

9. The laser probe assembly for an ophthalmic surgical procedure as set forth in claim 8 wherein the focusing element is a ball lens.

10. The laser probe assembly as set forth in claim 1 wherein the simultaneous laser beams exit from the side of the distal end of the handpiece.

* * * * *

UNITED STATES PATENT AND TRADEMARK OFFICE
CERTIFICATE OF CORRECTION

PATENT NO : 6,096,028
DATED : August 1, 2000
INVENTOR(S) : Sina Bahmanyar; Mark S. Jones It is certified that error appears in the above-identified patent and that said Letters Patent are hereby corrected as shown below:

On the title page item [54],
delete "Slot"
and substitute therefore --Spot--.

Signed and Sealed this

Seventeenth Day of April, 2001

Attest:

NICHOLAS P. GODICI

*Attesting Officer*   *Acting Director of the United States Patent and Trademark Office*